United States Patent [19]

Kaji

[11] 4,354,131
[45] Oct. 12, 1982

[54] SENSOR WITH CROSS-BASE MOUNTING PLATE

[75] Inventor: Kiyokane Kaji, Toyota, Japan

[73] Assignee: Toyota Jidosha Kogyo Kabushiki Kaisha, Aichi, Japan

[21] Appl. No.: 162,499

[22] Filed: Jun. 24, 1980

[30] Foreign Application Priority Data

Aug. 15, 1979 [JP] Japan .............................. 54-104302

[51] Int. Cl.³ .......................................... H01L 41/10
[52] U.S. Cl. .................... 310/328; 310/324; 73/654; 73/DIG. 4; 73/517 R
[58] Field of Search ............... 310/328, 324, 326, 329, 310/330; 73/35, 115, DIG. 4, 116, 119 A, 517 R, 654

[56] References Cited

U.S. PATENT DOCUMENTS

| | | | |
|---|---|---|---|
| 2,826,706 | 3/1958 | Sackett | 73/654 |
| 2,967,957 | 1/1961 | Massa | 310/324 |
| 3,056,298 | 10/1962 | Scholz | 73/115 |
| 3,633,053 | 1/1972 | Peters | 73/654 |
| 3,660,602 | 5/1972 | Thompson | 179/1 A |
| 4,096,735 | 6/1978 | Huntzinger et al. | 73/35 |
| 4,254,354 | 3/1981 | Keem | 73/35 |

Primary Examiner—Arthur T. Grimley
Assistant Examiner—D. L. Rebsch
Attorney, Agent, or Firm—Birch, Stewart, Kolasch & Birch

[57] ABSTRACT

A sensor for sensing a property, such as vibration, of a body, which includes an outer hollow tubular sensor casing, having open and closed ends and provided on its outside side with a protuberance adapted for connection to said body, such as by screwing; a base mounting plate mounted across the inner space in the tubular casing; a sensor element for producing an electrical output signal, mounted on the side of the base mounting plate remote from the open end of the tubular casing; an end closing member which closes the open end of the tubular casing; and an electrically conducting sensor lead structure, connected at its one end to the sensor element for receiving a sensor output electrical signal therefrom, and passing, in order therefrom, through an aperture in the base mounting plate, and through an aperture in the end closing member, to the outside of the sensor.

5 Claims, 3 Drawing Figures

SENSOR WITH CROSS-BASE MOUNTING PLATE

BACKGROUND OF THE INVENTION

The present invention relates to the field of sensors for converting various physical quantities into electrical signals, and more particularly relates to a particular construction for such a sensor.

In the prior art, many known sensors have been constructed for sensing various physical quantities, such as temperature, pressure, vibration, and the like, for automatic control and measurement in various mechanical devices, such as, for example, automobiles, and these sensor elements are generally contained in enclosed spaces within protective casings made of metal or plastic, so as to prevent ingress of moisture, oil, dust, or other undesirable pollutants thereinto. In such sensors, since they produce electrical output signals which indicate the value of the physical quantity which they are measuring, electrically conducting lead wires must be connected to their respective sensor elements for transmitting the output electrical signals generated in these sensor elements. Thus, in this case, if such a lead wire extends across the enclosed space containing the sensor element, there may arise a problem that such an electrically conducting lead wire may touch or otherwise interfere with the operation of the sensor element while the sensor is being used, thereby interfering with the performance characteristics of the respective sensor element and producing an erroneous indicated value of the physical quantity which the sensor should measure.

Further, in the particular case of the construction of a sensor element which senses vibration in a solid body, and is attached thereto by an attaching portion, problems have arisen with respect to the provision of a cheap and simple, yet reliable, construction arrangement for such a sensor, which can provide a sensor of long life and durability, and yet which is not extremely expensive or troublesome to manufacture.

Further, especially in the case of a vibration sensor to be used on an automobile engine, the provision of electrical connections for electrical lead wires to be connected to the sensor element has sometimes been prone to poor contact and other malfunctions, or to entry, over a long period of time, of water, dust, oil, or other contaminants into the connecting portions between said lead wires and the sensor.

SUMMARY OF THE INVENTION

Thus, an object of the present invention is to provide a construction for a sensor, in which an electrically conducting lead wire, for conducting electrical signals from the sensor element thereof, does not cross an enclosed space in which the sensor element is positioned.

A further object of the present invention is to provide a construction for a sensor which is strong, and which will last over a long period of use, and which is nevertheless simple in manufacture, and inexpensive.

A further object of the present invention is to provide such a construction for a sensor, in which the actual sensor element itself is positively protected by a fail safe structure from contamination by moisture or other contaminants such as dust and the like, without unduly increasing the production cost of the sensor.

Yet, another object of the present invention is to provide a system for attaching lead wires to such a sensor element, in which poor electrical connection between the lead wires and the sensor element, due to entry of moisture and other contaminants, may be satisfactorily prevented.

According to the present invention, these and other objects are attained by a sensor for sensing a property of a body, comprising an outer hollow tubular sensor casing, a first end of which is open and a second end of which is closed and is provided on its outside side with a protuberance adapted for connection to said body, a base mounting plate mounted across the inner space in said outer hollow tubular sensor casing, a sensor element for producing an electrical output signal, mounted on the side of said base mounting plate remote from said first open end of said outer hollow tubular sensor casing, an end closing member which closes said first open end of said outer hollow tubular sensor casing, and is fixedly mounted thereto, and an electrically conducting sensor lead structure, connected at its one end to said sensor element for receiving a sensor output electrical signal therefrom, and passing, in order therefrom, through an aperture in said base mounting plate, and through an aperture in said end closing member, to the outside of the sensor.

According to such a construction, since the electrically conducting lead element passes through the base mounting plate, and extends outwards on the opposite side of this base mounting plate from the side where the sensor element is mounted, this electrically conducting lead element does not cross the enclosed space in which the sensor element is mounted. Therefore, this electrically conducting lead element cannot touch the sensor element, or otherwise interfere with the operation of the sensor element, during use of the sensor.

Further, according to a particular detailed characteristic of the present invention, since the base mounting plate is secured in the outer hollow tubular sensor casing, across it, and is securely clamped in position therein by a hollow cylindrical slotted bracing ring, which is mounted within said outer hollow tubular sensor casing, and whose outer cylindrical face cooperates closely with the inner cylindrical face of said outer hollow tubular sensor casing, the axial end of said hollow cylindrical slotted bracing ring more remote from said connecting protuberance closely abutting the inner side of said closing member, and the end of said hollow cylindrical slotted bracing ring closer to said mounting protuberance closely abutting said base mounting plate, said base mounting plate being clamped in its position within said outer hollow tubular sensor casing between said hollow cylindrical slotted bracing ring and an annular step formed in the inner cylindrical surface of said outer hollow tubular sensor casing, the strong and reliable construction of such a sensor is advantageously facilitated.

Further, since the electrically conducting lead wire extends towards the side of the base mounting plate on which the closing member is provided, passing through the base mounting plate, the conduction of electrical signals out from the hollow tubular sensor casing is facilitated. Further, according to a particular feature of the present invention, since this closing member may be constructed as a connector for electrical connection of electric leads to the sensor, and may have a protective outer shell portion extending outwards around protruding portions of connector contact elements provided therein, electrical connection of electric leads to the sensor is facilitated.

BRIEF DESCRIPTION OF THE DRAWINGS

The present invention will become more fully understood from the following description of some preferred embodiments thereof, which is to be taken in conjunction with the accompanying drawings. It should be clearly understood, however, that the description of the embodiments, and the drawings, are all provided purely for the purposes of illustration and exemplification only, and are in no way to be taken as limitative of the scope of the present invention. In the drawings.

DESCRIPTION OF THE PREFERRED EMBODIMENTS

Figure 1:
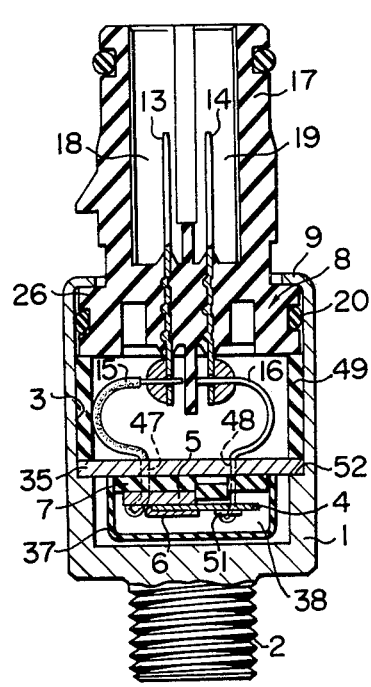
FIG. 1 is a part sectional view taken along the axis of a vibration sensor which is a first preferred embodiment of the present invention, showing its internal parts in detail.
Figure 2:
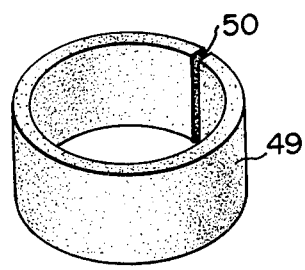
FIG. 2 is a perspective view of a hollow cylindrical axially slotted bracing ring used in the construction of the embodiment shown in FIG. 1.

Referring to the drawings, and particularly to FIGS. 1 and 2, there is illustrated in partial cross section in FIG. 1 a vibration sensor which is a first embodiment of the present invention. In FIG. 1, the reference numeral 1 denotes a metallic tubular casing which is formed as a hollow cylinder with a closed bottom. On the outside side of the closed bottom there is provided a screwed attachment protuberance 2, for mounting the vibration sensor to an internal combustion engine, for detecting knocking or pinging therein, or the like. The upper end in the drawing of the outer hollow cylindrical sensor casing 1 is open.

Inside the inner cavity 3 of the outer hollow cylinrical sensor casing 1 there is provided a piezoelectric sensor element 4, which is shaped as a plate member. This piezoelectric sensor element 4 is constructed of a piece of piezoelectric ceramic, such as $BaTiO_3$, and on opposite sides of this piezoelectric sensor element 4 there are attached electrically conducting first and second electrical contact plates 5 and 6, for picking up electrical signals therefrom produced by the bending thereof caused by vibration, in a per se well known way. The first electrical contact plate 5 is quite thick, as may be seen in the drawing, compared to the piezoelectic sensor element 4 and the second electrical contact plate 6, and this first electrical contact plate 5 is mounted to a base mounting plate 7, in such a manner that the piezoelectric sensor element 4 projects after the fashion of a cantilever. The base mounting plate 7 is attached to the lower surface in the drawing of a metallic cross base plate 35, which is arranged inside and across the inner space within the outer hollow cylindrical sensor casing 1, in a lower portion of the outer hollow cylindrical sensor casing 1, near the screwed attachment protuberance 2 thereof.

Further, the piezoelectric sensor element 4, the first and second electrical contact plates 5 and 6, etc., are covered over by the inner sensor protective cover 37, which fits over and cooperates with the base mounting plate 7, so as to define an inner protective container for the piezoelectric sensor element 4, said inner protective container being attached to the lower surface of said metallic cross base plate 35. Thus, this inner sensor protective cover 37 and the base mounting plate 7 between them define an enclosed sensor protective chamber 38, for protecting the piezoelectric sensor element 4 from damage due to ingress of dampness, dust, oil, or the like.

To each of the first and second electrical contact plates 5 and 6 there is attached one end of one of the connecting lead wires 15 and 16, respectively. The connecting lead wire 16 is in fact, attached to a connecting metallic piece 51, which is substantially formed in one piece with the second electrical contact plate 6, although it is not clearly so visible in the drawing. These connecting lead wires 15 and 16 extend in the upwards direction in the drawing, through holes pierced through the base mounting plate 7, and through holes 47 and 48 pierced through the metallic cross base plate 35, respectively, and the other outer ends of these connecting lead wires 15 and 16 are connected, respectively, to the lower ends of first and second connector contact elements 13 and 14, with a certain amount of free play or slack being left as remaining in the connecting lead wires 15 and 16, between their connecting ends to the first and second connector contact elements 13 and 14 respectively, and the places where they respectively pass through the holes 47 and 48 in the metallic cross base plate 35.

The first and second connector contact elements 13 and 14 are mounted solidly within a connector housing 8, by insert moulding or the like provided around irregular portions of these first and second connector contact elements 13 and 14. This connector housing 8 is mounted so as to close the open upper end of the outer hollow cylindrical sensor casing 1, and closely cooperates with this open end. Between the connector housing 8 and the metallic cross base plate 35, abutting to each of them, there is mounted a hollow cylindrical slotted bracing ring 49, which is a sleeve spacing member, for a purpose which will be explained hereinafter. This hollow cylindrical slotted bracing ring 49 is provided with a longitudinal or axial slot 50, so that it may be fitted between the connector housing 8 and the metallic cross base plate 35, after the connecting lead wires 15 and 16 have been connected to the first and second connector contact elements 13 and 14 respectively, by these connecting lead wires 15 and 16 being passed through the slot 50.

The upper ends in the drawing of the first and second connector contact elements 13 and 14 protrude upwardly past the lower body portion of the connector housing 8 which closes the open end of the outer hollow cylindrical sensor casing 1 for a certain distance, and are surrounded by a connector contact element protective outer shell portion 17 of the connector housing 8, which defines two connector contact holes 18 and 19, which surround, respectively, the first and second connector contact elements 13 and 14, with a space being left between this shell portion 17 and these first and second connector contact elements 13 and 14. Thus, when electrical connection of output lead wires, not shown in the drawing, is made to these first and second connector contact elements 13 and 14 by a connector adaptor, not shown in the drawings, of a per se well known sort, which is connected to said output lead wires, this connector contact element protective outer shell portion 17 serves to prevent ingress of dampness, dust, oil, and the like, which might otherwise disturb the quality of the electrical contact made between the first and second connector contact elements 13 and 14 and said output lead wires.

The lower body portion of the connector housing 8, which, as explained above, closes the open upper end in the drawings of the outer hollow cylindrical sensor casing 1, is engaged to the inner cylindrical surface 3 of the casing 1, and is fixed thereto, by the upper end 9 of the casing 1 being crimped over so that it positively engages with a step 26 formed on said connector housing lower body portion. Further, a sealing O ring 20 is located in between the connector housing lower body portion and the inner cylindrical surface 3 of the hollow cylindrical sensor casing 1, in an annular circumferential groove formed on the outer cylindrical surface of the connector housing lower body portion, so as to seal the gap therebetween, and so as resiliently to improve the physical connection therebetween, as well as to prevent ingress of dampness, oil, dust, or the like to the internal space of the sensor housing, where such pollutants might interfere with the functioning of the piezoelectric sensor element 4.

In the above described vibration sensor, the connecting lead wires 15 and 16, which are connected to the piezoelectric sensor element 4, are directly led out through the base mounting plate 7 and the metallic cross base plate 35, so that they are not required to cross the internal space in the enclosed sensor protective chamber 38. Thereby, there is no risk that these connecting lead wires 15 and 16 should undesirably touch or interfere with the piezoelectric sensor element 4. This increaes the reliability of the shown sensor.

Further, the provision of slack in the connecting lead wires 15 and 16, between their ends where they are attached, respectively, to the first and second connector contact elements 13 and 14, and their portions where they pass through, respectively, the holes 47 and 48 provided in the metallic cross base plate 35, ensures that, because these extended portions of the connecting lead wires 15 and 16 are not tight, no undesirable disturbance can be transmitted thereby by pulling on the piezoelectric sensor element 4. This, again, increases the reliability of the shown sensor.

It is also to be noted that, in the sensor device according to the first embodiment of the present invention explained above, the provision of the inner sensor protective cover 37, which defines the enclosed sensor protective chamber 38, ensures a double or fail safe protection for the piezoelectric sensor element 4 against ingress of dampness, oil, dust, or other pollutants which might otherwise harm its efficiency during use. This inventive concept is described more fully, and claimed, in copending U.S. patent application Ser. No. 162,101, filed by the same applicant and assigned to the same assignee as the present application.

The system of assembling the vibration sensor, shown in FIG. 1, which is a first embodiment of the present invention, will now be explained.

First, the base mounting plate 7, which supports the piezoelectric sensor element 4, is attached by adhesive, rivetting, or the like, to one surface of the metallic cross base plate 35.

Then the one ends of the connecting lead wires 15 and 16 are soldered, respectively, to the first and second electrical contact plates 5 and 6. In the shown embodiment, in fact, the connecting lead wire 16 is soldered to a metallic connecting piece 51 which is substantially formed in a body together with the first electrical contact plate 6.

Then the other ends of these connecting lead wires 15 and 16 are inserted from the bottom side as shown in FIG. 1, into holes, which are pierced in the base mounting plate 7, and through these holes are inserted into the holes 47 and 48, which correspond thereto, and which are pierced in the metallic cross base plate 35. The connecting lead wires 15 and 16 are then pulled through these holes 47 and 48, respectively, and are led upwards.

Then, the inner sensor protective cover 37 is fitted over the base mounting plate 7, closely cooperating therewith, and is attached to the lower surface of the metallic cross base plate 35, so as to form the closed sensor protective chamber 38 in cooperation with said base mounting plate 7, and so as to positively protect the piezoelectric sensor 4 against ingression of dampness, oil, dust, or the like.

Then, the connector housing 8, which has been formed integrally with the first and second connector contact elements 13 and 14 embedded therein as shown in FIG. 1, is approached to the assembly above described, and the other or upper ends of the connecting lead wires 15 and 16 are, respectively, soldered, or fixed in some other appropriate fashion such as by crimping, to the lower ends of said first and second connector contact elements 13 and 14.

Next, the intermediate portions of the connecting lead wires 15 and 16, between their upper ends which are soldered to the first and second connector contact elements 13 and 14 and the points where they pass through the holes 47 and 48 in the metallic cross base plate 35, i.e., their slack portions, are extended by pulling apart the connector housing 8 and the metallic cross base plate 35, and the hollow cylindrical axially slotted bracing ring 49, which is illustrated in detail in FIG. 2, is slipped over and around these extended wire portions, by passing these extended wire portions through the axially extending slot 50 thereof.

Next, the conjoined assembly of these three units, i.e., the unit comprising the metallic cross base plate 35, the piezoelectric sensor 4, etc., the unit consisting of the hollow cylindrical slotted bracing ring 49, and the unit comprising the first and second connector contact elements 13 and 14 and the connector housing 8, is approached to and inserted into the outer hollow cylindrical sensor casing 1, with the metallic cross base plate 35 entering thereinto, and then the metallic cross base plate 35 is pushed into the hollow cylindrical sensor casing 1 until it seats snugly on a step 52, which is formed on the hollow cylindrical sensor casing inner surface 3. Thus, the inner sensor protective cover 37, which defines the enclosed sensor protective chamber 38 in cooperation with the base mounting plate 7, is snugly received within the bottom cavity of the outer hollow cylindrical sensor casing 1, near its closed end.

The hollow cylindrical axially slotted bracing ring 49 is then seated, as shown in FIG. 1, against the upper surface of the metallic cross base plate 35, and then the lower surface of the connector housing body portion 8 is seated against the upper end of this hollow cylindrical axially slotted bracing ring 49, and, after the sealing O ring 20 has been fitted onto the body portion of the connector housing 8, and, while force is being applied to push the connector housing 8 into the outer hollow cylindrical sensor casing 1, so as to clamp all the aforementioned parts together, the upper end 9 of said outer hollow cylindrical casing 1 is bent over or crimped, so that it may engage with the shoulder portion 26 of the connector housing 8 and positively hold said connector housing 8 into the cavity in the outer hollow cylindrical sensor casing 1.

Thus, the abovementioned three assemblies are positively held together by the crimped shoulder portion 9, and, by the clamping of the hollow cylindrical slotted bracing ring 49 between the upper surface of the metallic cross base plate 35 and the lower surface of the connector housing 8, said metallic cross base plate 35 and said connector housing 8 being thus clamped between said crimped over shoulder securing portion 9 and said step 52, and the secure and long lasting integral connection of all these parts is positively assured.

Figure 3:
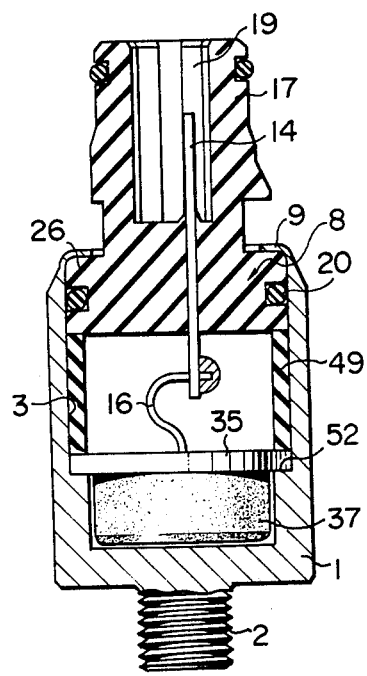
FIG. 3 is a part sectional view, similar to FIG. 1, illustrating a vibration sensor which is a second preferred embodiment of the present invention.

FIG. 3 shows a vibration sensor, which is a second preferred embodiment of the present invention, and which is shown in a longitudinal part sectional view, similar to FIG. 1. In this second preferred embodiment, the first electrical contact plate 5, which is attached to the sensor element 4, is directly connected to the metallic cross base plate 35, so that this connection of the sensor element 4 is grounded to the outer hollow cylindrical sensor casing 1, which is made of metal. Therefore, only the connecting lead wire 16 and only one connector contact element 14 need be provided, instead of the two connector contact elements 13 and 14 provided in the first embodiment.

In this second embodiment, as in the previously described first embodiment, a certain amount of free play or slack is left in the connecting lead wire 16, between its upper end connected to the connector contact element 14, and its intermediate portion passing through the metallic cross base plate 35, so as to ensure that the piezoelectirc sensor element 4 is not undesirably disturbed by pulling on this lead wire 16.

Again, in this embodiment, the portion of the connecting lead wire 16, which is inside the enclosed sensor protective chamber 38 defined by the inner sensor protective cover 37 and the base mounting plate 7, does not cross this enclosed sensor protective chamber 38, and therefore there is no risk that this portion of the connecting lead wire 16 should undesirably interfere with the operation of the piezoelectric sensor element 4.

Further, by the hollow cylindrical slotted bracing ring 49 being clamped between the metallic cross base plate 35 and the connector housing body portion 8, i.e., between the step 52 in the outer hollow cylindrical sensor casing inner surface 3 and the turned over or crimped portion 9 of the outer hollow cylindrical sensor casing 1, the same benefits and advantages are obtained as were obtained in the first described embodiment. Further, by the provision of the upwardly extending connector contact element protective outer shell portion 17 around the upwardly projecting portion of the connector contact element 14, with a space 19 being left therebetween, the same functions and advantages are obtained as were obtained in the first preferred embodiment.

Although the present invention has been shown and described in terms of some preferred embodiments thereof, and in language more or less specific with regard to structural features thereof, and with reference to the illustrative drawings, it should be understood that in any particular embodiment of the present invention various changes, modifications, and omissions of the form and the detail thereof can be made by a person skilled in the art, without departing from the essential scope of the invention.

I claim:

1. A sensor for sensing vibration of a body, comprising:
   an outer hollow tubular sensor casing having a stepped bore providing a shoulder portion, a first end of which is open and a second end of which is closed, said closed end being provided on the outside side thereof with a protuberance for connection to said body;
   a cross base plate mounted across the inner space in said outer hollow tubular sensor casing and supported by said shoulder portion;
   a vibration sensor element for producing an electrical output signal, mounted on the side of said cross base plate remote from said first open end of said outer hollow tubular sensor casing;
   a unitary end connector housing closing member including a lower body cover plate portion which closes said first open end of said outer hollow tubular sensor casing firmly mounted thereto, and a connector contact element protective outer shell portion extending outwardly from said lower body cover plate portion through said open end of said outer hollow tubular sensor casing defining a cavity space;
   a tubular spacing means for spacing said cover plate portion of said closing member from said cross base plate so as to provide an intermediate space therebetween;
   at least one electrically conducting lead wire having an inner end portion connected to said vibration sensor element for receiving a sensor output electrical signal therefrom and an outer end portion passing substantially in an airtight manner through said cross base plate; and
   an electrical connector element extending through said cover plate portion of said connector housing into said cavity space defined by said connector contact element protective outer shell portion and connected to said outer end portion of said at least one electrically conducting lead wire on the side of said cover plate portion of said closing member remote from said connector contact element protective outer shell portion within said intermediate space.

2. A sensor according to claim 1, wherein said tubular spacing means is a hollow cylidnrical slotted ring provided with a longitudinal slot.

3. A sensor according to claim 1, further comprising a cup-shaped inner casing mounted to the side of said cross base plate remote from said first open end of said outer hollow tubular sensor casing so as to enclose said sensor element therein.

4. The sensor according to claim 1, further comprising a means for fixing said lower body cover plate portion of said connector housing to the inner cylindrical surface of said hollow cylindrical sensor casing.

5. The sensor according to claim 4, further including a sealing means fitted onto the lower body cover plate portion of said connector housing for further providing a contaminant-free configuration.

* * * * *